(12) United States Patent
Khan et al.

(10) Patent No.: US 8,191,802 B2
(45) Date of Patent: *Jun. 5, 2012

(54) AEROSOL

(75) Inventors: Ayub Ibrahim Khan, Cincinnati, OH (US); Su-Yon McConville, Mason, OH (US); Christopher Luke Leonard, Mason, OH (US); Scott Edward Smith, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1338 days.

This patent is subject to a terminal disclaimer.

(21) Appl. No.: 11/092,088

(22) Filed: Mar. 29, 2005

(65) Prior Publication Data

US 2005/0224524 A1 Oct. 13, 2005

Related U.S. Application Data

(60) Provisional application No. 60/557,355, filed on Mar. 29, 2004.

(51) Int. Cl.
*B05B 1/14* (2006.01)
*B05B 1/00* (2006.01)

(52) U.S. Cl. .................. 239/565; 239/600; 239/548

(58) Field of Classification Search .............. 239/5, 296, 239/337, 347, 372, 414, 543, 565, 527, 573, 239/579, 306, 106, 334; 222/145, 135, 148, 222/190, 330, 531
See application file for complete search history.

(56) References Cited

U.S. PATENT DOCUMENTS

| | | | | |
|---|---|---|---|---|
| 3,342,382 A | | 9/1967 | Huling | |
| 3,401,888 A | | 9/1968 | Sutter | |
| 3,406,913 A | * | 10/1968 | Frangos | .................. 239/543 |
| 3,415,426 A | * | 12/1968 | Kleveland | ................ 222/402.11 |
| 3,504,862 A | | 4/1970 | Lowry | |
| 3,628,733 A | * | 12/1971 | Kahn | ............... 239/337 |
| 3,767,125 A | * | 10/1973 | Gehres et al. | .................. 239/552 |
| 4,168,021 A | * | 9/1979 | Hardouin et al. | .............. 222/394 |
| 4,239,407 A | | 12/1980 | Knight | |
| 5,249,747 A | * | 10/1993 | Hanson et al. | ................. 239/373 |
| 5,516,045 A | | 5/1996 | Baudin | |
| 5,730,332 A | * | 3/1998 | Zimmerhackel | .............. 222/148 |
| 5,813,785 A | | 9/1998 | Baudin et al. | |
| 5,890,661 A | * | 4/1999 | Crampton et al. | ............. 239/544 |
| 6,158,674 A | * | 12/2000 | Humphreys | ................. 239/333 |

(Continued)

FOREIGN PATENT DOCUMENTS

| | | |
|---|---|---|
| DE | 1817056 | 7/1969 |
| DE | 2925435 A1 | 1/1981 |
| EP | 0077572 A | 4/1983 |
| EP | 0245822 A | 11/1987 |

*Primary Examiner* — Len Tran
*Assistant Examiner* — James Hogan
(74) *Attorney, Agent, or Firm* — Andrew J. Hagerty

(57) ABSTRACT

A spray head for attachment to an aerosol container containing pressurized product is provided, the spray head comprising conduit means, more than one separate spray outlet and a splitting chamber for diverting the flow to the spray outlets, wherein the conduit means comprise inlet means for attachment to a valve stem of the aerosol spray unit and conduit outlet means which are in direct fluid communication with the splitting chamber, wherein the splitting chamber is in fluid communication with the spray outlets and wherein, for each spray outlet, the ratio, L1/L2, of the distance (L1) between the conduit outlet means and the spray outlet to the distance (L2) between the inlet means and the spray outlet is in the range 0.01 to 0.6.

11 Claims, 2 Drawing Sheets

U.S. PATENT DOCUMENTS

Figure 1:
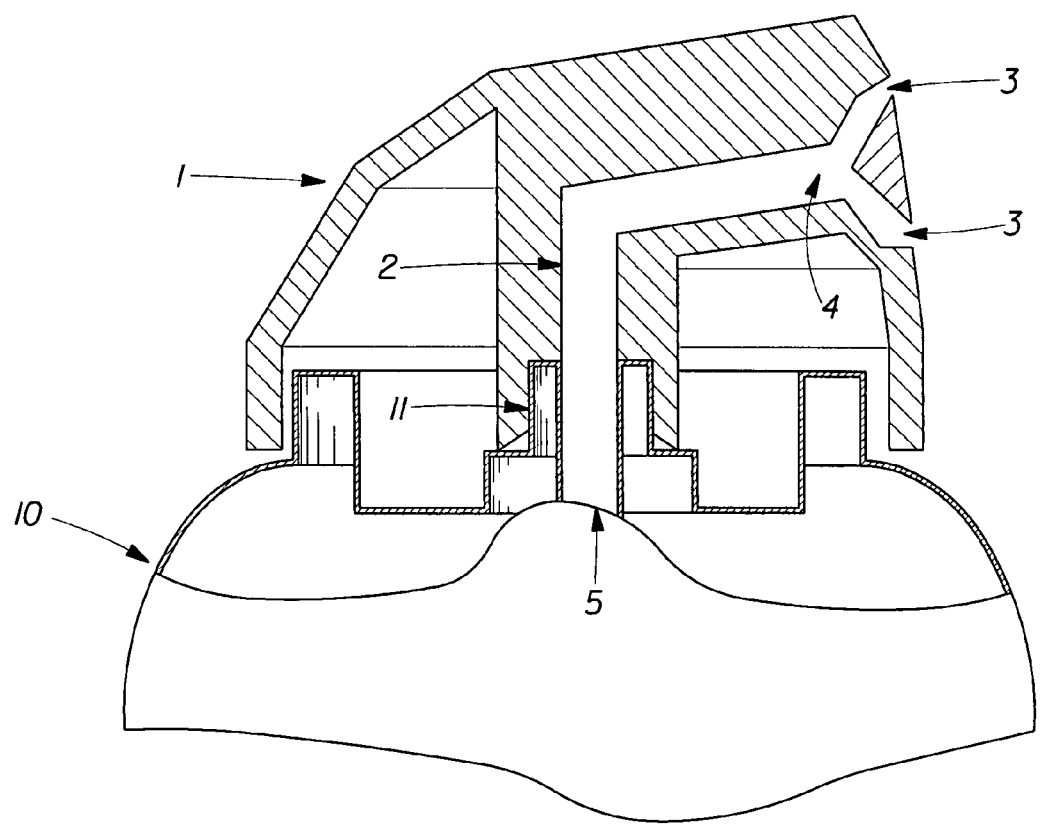
Figure 2:
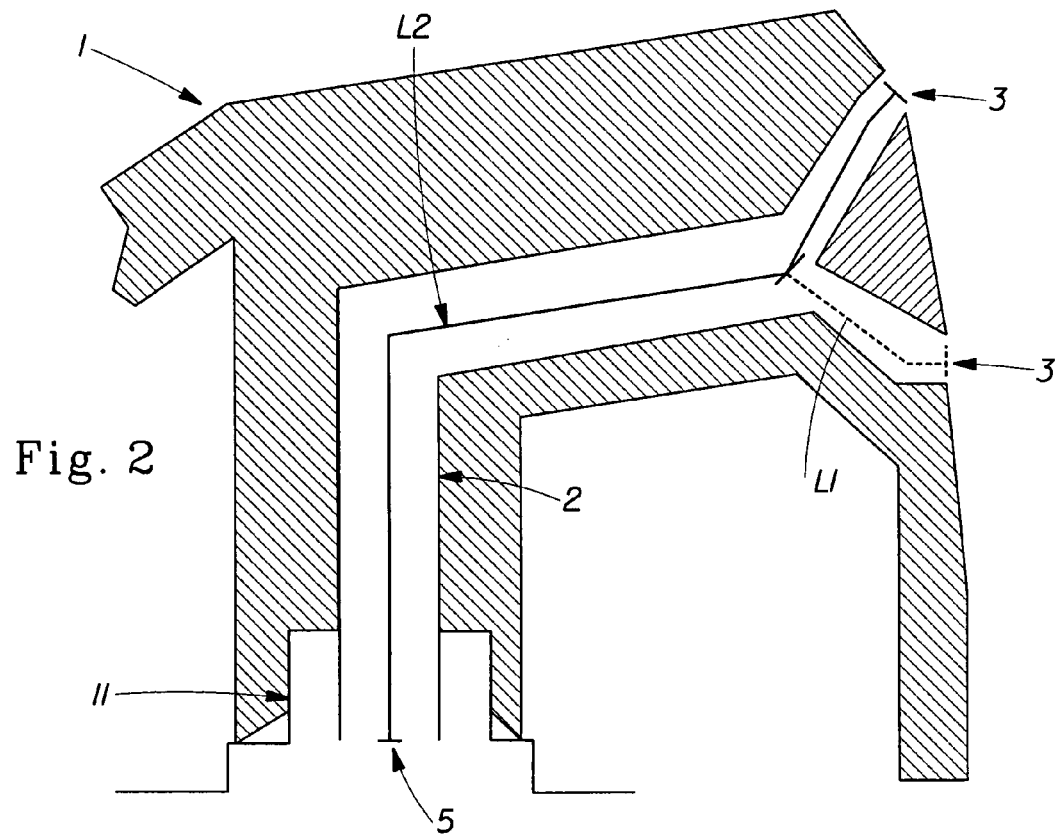
Figure 3:
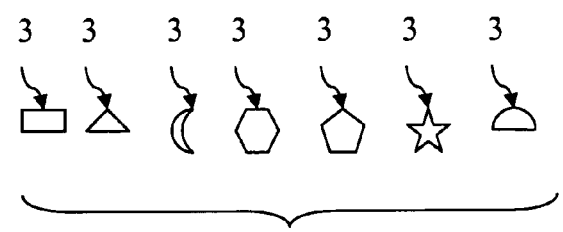

| | | | |
|---|---|---|---|
| RE38,023 E * | 3/2003 | De Laforcade | 239/337 |
| 6,817,493 B1 * | 11/2004 | Parsons et al. | 222/402.1 |
| 6,971,557 B2 * | 12/2005 | Mather et al. | 222/402.13 |
| 2004/0195374 A1 | 10/2004 | Parsons et al. | |

* cited by examiner

AEROSOL

CROSS REFERENCE TO RELATED APPLICATIONS

This application claims the benefit of U.S. Provisional application Ser. No. 60/557,355 (Case CM2835FP), filed on Mar. 29, 2004.

FIELD

The present invention relates to an aerosol spray head, an aerosol spray unit comprising the aerosol spray head and a process for spraying pressurised product.

BACKGROUND

One conventional approach to dispensing a product onto a target application surface is via atomisation of that product. One way of achieving atomisation is to combine the product with a propellant (compressed gas) in a pressurized unit having a dispensing valve fluidly connected to a dispensing outlet. On opening the dispensing valve, the product is forced therethrough and dispensed via the outlet in an atomized form onto the target application surface.

The present inventors have established, however, that current atomization technology generally does not deliver a satisfactory product distribution onto the target area. In particular, the distribution is observed to be uneven, with, for example, increased deposition occurring in the centre and correspondingly reduced deposition towards the extremities of the target site. In addition to the uneven spread of active agent and resulting uneven achievement of benefit across the target site, increased deposition in one area, for example the centre, may additionally result in the formation of unsightly residues and unpleasant cooling in that region of the consumer's skin, due to the increased amounts of product deposited there and increased amounts propellant evaporating at that location.

In addition to the above-mentioned shortcomings, a single outlet spray head also places physical limitations on the composition which may be sprayed. In particular, high viscosity compositions may not be practically sprayed, because insufficient energy may be retained in such a fluid under typical pressurisation conditions for it to become sufficiently atomised on leaving the spray outlet.

With reference to U.S. Pat. No. 3,767,125, a multi-outlet spray head is proposed for spraying dry powder aerosols.

With reference to U.S. Pat. No. 5,516,045, an alternative multi-outlet spray head is disclosed, especially for spraying hair lacquer.

It would be advantageous to provide a spray head which overcomes the disadvantages of spray heads disclosed in the prior art.

SUMMARY

According to a first aspect of the invention a spray head for attachment to an aerosol container containing pressurised product is provided, the spray head comprising conduit means, more than one separate spray outlet and a splitting chamber for diverting the flow to the spray outlets, wherein the conduit means comprise inlet means for attachment to a valve stem of the aerosol spray unit and conduit outlet means which are in direct fluid communication with the splitting chamber, wherein the splitting chamber is in fluid communication with the spray outlets and wherein, for each spray outlet, the ratio, L1/L2, of the distance (L1) between the conduit outlet means and the spray outlet to the distance (L2) between the inlet means and the spray outlet is from 0.01 to 0.6.

According to a second aspect of the invention, an pressurised aerosol spray unit is provided, having a spray head as defined in the first aspect of the invention.

According to a third aspect of the invention, a portable pressurised aerosol spray unit is provided, having a spray head as defined in the first aspect of the invention.

According to a fourth aspect of the invention, a process for spraying a pressurised product is provided, comprising the steps of spraying said product through a spray head according to the first aspect of the invention, such that the product has a Reynolds Number of at least 3000 as it leaves said spray outlets.

These and other features, aspects, and advantages of the present invention will become evident to those skilled in the art from a reading of the present disclosure.

BRIEF DESCRIPTION OF THE DRAWINGS

While the specification concludes with claims which particularly point out and distinctly claim the invention, it is believed the present invention will be better understood from the following description of preferred embodiments taken in conjunction with the accompanying drawings, in which like reference numerals identify identical elements and in which:

FIG. 1 is a cross-sectional view of a spray head according to the invention

FIG. 2 is an enlarged cross-sectional view of the important parts of a spray head according to the invention.

FIG. 3 is an enlarged view of several exemplary spray outlet cross-sectional shapes.

DETAILED DESCRIPTION

While the specification concludes with claims which particularly point out and distinctly claim the invention, it is believed the present invention will be better understood from the following description.

All weights, measurements and concentrations herein are measured at 25° C. on the composition in its entirety, unless otherwise specified.

Unless otherwise indicated, all percentages of compositions referred to herein are weight percentages of the total composition (i.e. the sum of all components present) and all ratios are weight ratios.

Unless otherwise indicated, the content of all literature sources referred to within this text are incorporated herein in full by reference.

Except where specific examples of actual measured values are presented, numerical values referred to herein should be considered to be qualified by the word "about".

As has been discussed, a limitation of traditional aerosol spray head configurations is that they may produce an uneven distribution of product on the target site. In addition, the viscosity of the product to be sprayed may be practically constrained to remain below a certain level.

By introducing instability into the fluid flow at an early stage it is possible to atomize products with greater viscosities and, at the same time, improve the product distribution on the target site. The replacement of a single spray outlet by multiple outlets may assist in introducing that instability, because, for a given volume flow of product, the size of the shear interface (i.e. the total outlet perimeter size) is greater for multiple outlets than for a single outlet. Without wishing to be bound by theory, it is believed that this measure may prevent the formation of a smooth film structure just outside the outlet where the product commences its trajectory to the target site. The disadvantage of a smooth film structure is that it may propagate a relatively coarse atomization in the final stage before the product reaches the target site, with the drops at the center of the spray being larger than those near the periphery. It is in the final stage of the spray formation where an instability in the system may help disintegrate the product into ligaments and then further into drops to form a highly atomised spray and an improved drop distribution.

In addition, in a multi-outlet system, it is observed that, following the split in the flow to channel fluid to the separate orifices, changes to the separate flows may occur such that there may be differences, for example, in viscosity or other parameters, between what is sprayed from one outlet and what is sprayed from the other or others. If there are differences between the individual sprays immediately after they leave their respective spray outlets, then that may translate into differences in product distribution at the target site. Without wishing to be bound by theory, it is believed that these changes may be brought about by manufacturing limitations. In other words, it is very difficult to ensure that the ducts along which the separate flows travel are identical. To counter this, it has been found to be beneficial to locate the point at which the flow splits to travel to the two or more separate spray outlets close to the spray outlets such that most of the flow within the spray head occurs prior to the split. To be more specific and as set out above, it has been found that it is beneficial to design the spray head (1) such that the ratio, L1/L2, for each spray outlet (3), of the distance (L1) between the conduit outlet means and the spray outlet (3) to the distance between the inlet means (5) and the spray outlet (3) is from 0.01 to 0.6, preferably from 0.015 to 0.4 and more preferably from 0.02 to 0.4.

In the event that the conduit and/or ducts leading to the spray outlets have a non-constant cross-sectional area such that either or both of L1 and L2 may vary depending on the line of measurement, then the measurements must be made along the centre line connecting the centres of the inlet means (5), the conduit outlet means and the respective spray outlet (3).

In one preferred embodiment, at least one of the spray outlets has a ratio L1/L2 which is different from the other or others. In another preferred embodiment, all the spray outlets have the same ratio L1/L2.

Advantageously, at least one of the spray outlets and preferably all of the spray outlets are non-circular. Employing non-circular spray outlets may additionally assist in introducing early instability into the flow, thereby improving distribution at the target site.

As used herein, the term "circle" means a closed plane curve every point of which is equidistant from a fixed point within the curve and the word "circular" shall be interpreted accordingly.

With reference to FIG. 3, the spray outlets (3) may have any non-circular shape, but advantageously have a cross-sectional shape selected from the group consisting of polygonal, semi-circular, crescent, stellate and mixtures thereof. If polygonal, then each polygonal cross-sectional shape may advantageously be selected from the group consisting of polygons having from three to ten sides. Preferably, the polygons are selected from the group consisting of triangular, rectangular, pentagonal, hexagonal and mixtures thereof.

The spray head (1) according to the invention may have any number of spray outlets (3) above two, but preferably has from 2 to 36 and more preferably from 3 to 12 spray outlets (3).

According to a second aspect of the invention, an aerosol spray unit (10) is provided comprising a pressurised product to be dispensed and having a spray head (1) according to the first aspect of the invention.

As used herein, the term "spray unit" means a pressurised aerosol canister, comprising a valve, the valve stem of which extends from the canister, typically at the top. Such canisters typically have a volume up to 1000 ml, though more typically below 200 ml and are typically pressurised at 103 kPa to 552 kPa (15 to 80 psi), more typically less than 414 kPa (60 psi).

As used herein, the term "product" means all components of the composition or mixture contained within the spray unit, including all active agents, all carrier materials and all propellant.

Preferably, the product to be dispensed is a cosmetic product, more preferably it is selected from the group consisting of antiperspirants, deodorants and mixtures thereof.

If the product to be dispensed is an antiperspirant, then it may comprise antiperspirant active particulates and a carrier such that the antiperspirant active particulates are not soluble in the carrier. Alternatively, the antiperspirant active may be solubilised in the carrier.

According to a third aspect of the invention, a portable aerosol spray unit (10) is provided comprising a pressurised product to be dispensed and a spray head (1) according to the first aspect of the invention.

As used herein, the term "portable" used in relation to an aerosol spray unit means that it may readily be transported in one hand by a single adult person of ordinary strength.

According to a fourth aspect of the invention, a process for spraying a pressurised product is provided comprising the steps of spraying said product through a spray head having at least two separate spray outlets (3), wherein at least one of the spray outlets (3) has a non-circular cross-section, such that the product has a Reynolds Number of at least 3000 as it leaves said spray outlets (3).

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A spray head for attachment to an aerosol spray unit containing pressurised product, the spray head comprising conduit means, more than one separate spray outlet and a splitting chamber for diverting the flow to the spray outlets wherein the conduit means comprise inlet means for attachment to a valve stern of the aerosol spray unit and conduit outlet means which are in direct fluid communication with the splitting chamber wherein the splitting chamber is in fluid communication with the spray outlets and wherein, for each spray outlet, the ratio, L1/L2, of the distance (L1) between the point at which the flow splits to travel to the separate spray outlets and the spray outlet to the distance (L2) between the inlet means and the spray outlet is from 0.015 to 0.4.

2. The spray head of claim 1 wherein at least one of the spray outlets has a ratio L1/L2 which is different from the other or others.

3. The spray head of claim 1 wherein all the spray outlets have the same ratio L1/L2.

4. The spray head of claim 1 wherein at least one of the spray outlets has a non-circular cross-section.

5. The spray head of claim 1 wherein all the spray outlets have a non-circular cross-sectional shape.

6. The spray head of claim 1 wherein one or more of the spray outlets have a cross-sectional shape selected from the group consisting of polygonal, semi-circular, crescent, stellate and mixtures thereof.

7. The spray head of claim 6 wherein each polygonal cross-sectional shape is selected from the group consisting of polygons having from three to ten sides.

8. The spray head of claim 7 wherein each polygonal cross-sectional shape is selected from the group consisting of triangular, rectangular, pentagonal, hexagonal and mixtures thereof.

9. The spray head of claim 1 having from 2 to 36 outlets.

10. The spray head of claim 1 wherein one or more of the spray outlets have a semi-circular cross-sectional shape.

11. The spray head of claim 1 having from 3 to 12 spray outlets.

* * * * *